United States Patent
Kreier et al.

(10) Patent No.: US 6,250,159 B1
(45) Date of Patent: Jun. 26, 2001

(54) CHARACTERIZATION OF OBJECTS BY MEANS OF ULTRASONIC WAVES

(75) Inventors: Peter Kreier, Eschlikon; August Kälin, Bonnstetten, both of (CH)

(73) Assignee: Hans-Ulrich Ramseier, Munsingen (CH)

(*) Notice: Subject to any disclaimer, the term of this patent is extended or adjusted under 35 U.S.C. 154(b) by 0 days.

(21) Appl. No.: 09/180,346
(22) PCT Filed: Apr. 14, 1997
(86) PCT No.: PCT/CH97/00145
§ 371 Date: Apr. 12, 1997
§ 102(e) Date: Apr. 12, 1997
(87) PCT Pub. No.: WO97/40373
PCT Pub. Date: Oct. 30, 1997

(30) Foreign Application Priority Data

Apr. 18, 1996 (CH) ........................................ 984/96

(51) Int. Cl.⁷ .................................................. G01N 29/04
(52) U.S. Cl. ............................................................ 73/602
(58) Field of Search .............................. 73/602, 644, 597, 73/598, 643, 642

(56) References Cited

U.S. PATENT DOCUMENTS

| | | | |
|---|---|---|---|
| 4,545,248 | * 10/1985 | Kitada et al. | 73/597 |
| 5,247,937 | 9/1993 | Ophir | 73/598 |
| 5,369,997 | 12/1994 | Roberts | 128/661.03 |
| 5,513,531 | * 5/1996 | Sapia et al. | 73/602 |
| 5,661,241 | * 8/1997 | Harth, III et al. | 73/622 |
| 5,723,791 | * 3/1998 | Koch et al. | 73/597 |

FOREIGN PATENT DOCUMENTS

| | | |
|---|---|---|
| 44 14 030 | 8/1995 | (DE) . |
| 0 574 964 | 12/1993 | (EP) . |

* cited by examiner

Primary Examiner—Daniel S. Larkin
Assistant Examiner—Rose M. Miller
(74) Attorney, Agent, or Firm—Oppedahl & Larson LLP

(57) ABSTRACT

To characterize an object (3) to be measured, for example to gauge the thickness ($d_7$) of a layer (7) borne by a substrate (4), an ultrasonic wave (8.1) is transmitted by a measuring device (1). Echo impulses (8.2, 8.5) reflected by boundary surfaces (5, 10) of the object (3) to be measured are detected by the measuring device (1); the measuring signal is digitalised and subjected to an evolution analysis in the time domain. The evolution analysis uses an algorithm which is computation-efficient by orthogonalisation and implemented search strategy. The characteristics of the object to be measured, for example the thicknesses, are determined from the delay time differences of the echo waves (8.2, 3.5).

24 Claims, 6 Drawing Sheets

CHARACTERIZATION OF OBJECTS BY MEANS OF ULTRASONIC WAVES

Figure 1:
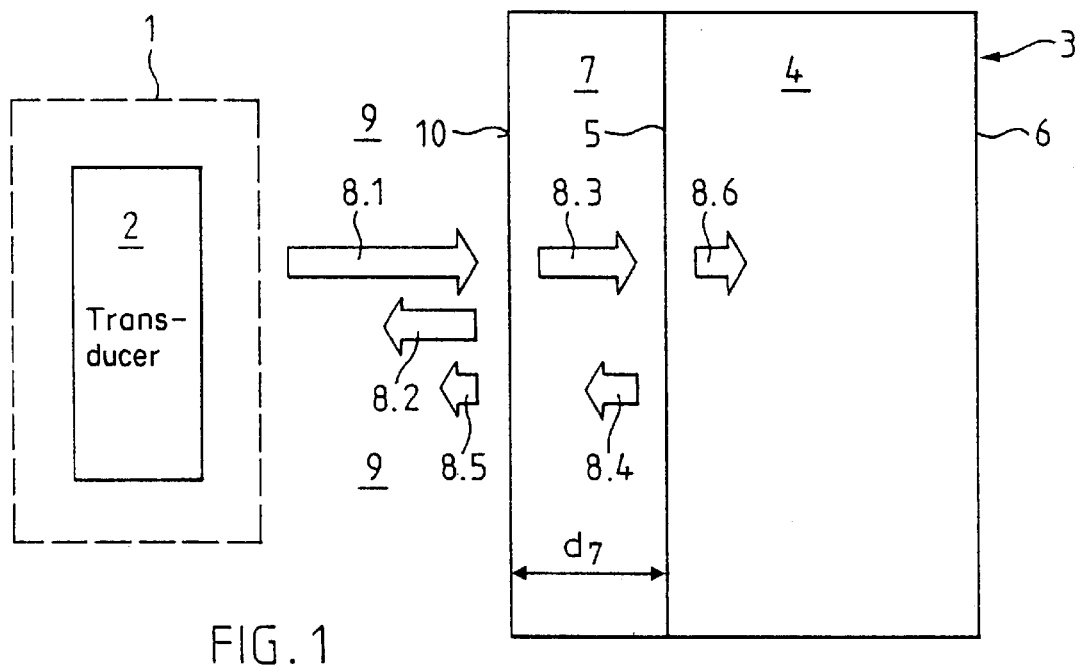

The invention relates to a method and a measuring device for characterising objects by means of ultrasound according to the precharacterising portions of the independent claims. In particular the thickness of walls, of layers on substrates and in composite layers can be measured, as can heights of steps on surfaces, as well as surface profiles.

When an ultrasonic wave hits a boundary surface of two media of different acoustic impedance, then in general it is partly reflected. This phenomenon is inter alia exploited for thickness gauging. An ultrasonic impulse is admitted to the object to be measured, for example a layer carried by a substrate. Then the ultrasonic impulses (echo impulses) which have been reflected at the front and rear of the object are detected as a measuring signal. From the delay time difference $\Delta t$ between the two echo impulses, the thickness d of the object can be calculated by suitable calibration, e.g. if the acoustic velocity c is known:

$$d=c\Delta t/2.$$

Conversely, if the object thickness d is known and the delay time difference $\Delta t$ has been measured, the acoustic velocity c can be calculated.

Such an ultrasound measuring signal can be taken as convolution of a measuring-object-dependent reflection sequence with a system reply depending on the measuring system. Accordingly the detected measuring signals are not ideal, sharp peaks (delta functions) but prolonged high-frequency impulses, due to the limited bandwidth of the test system. Inter alia, this results in the following difficulties for the thickness gauging described above. Where the requirements for accuracy are high, the delay time difference $\Delta t$ must partly be determined with an accuracy below the duration of an ultrasonic impulse, for example by means of a curve adaptation function or by means of a characteristic position (threshold value, zero passage, slope) of the ultrasound impulses. In the case of small thicknesses, i.e. in the case of small delay-time differences, the two echoes overlap, resulting in difficulties in their resolution. The relative terms "thin", "small" thickness of the layer to be measured or "high" accuracy which are used here, are always to be understood in relation to the high-frequency impulse duration (carrier frequency or centre frequency) applicable depending on the materials and methods. These difficulties manifest themselves increasingly in technologically interesting thickness-gauging problems, due to the ever thinner layers applied and/or due to acoustic delay specific to the material and the medium of propagation, which acoustic delay increases at higher frequencies.

For example, printed patent specification DE 44 14 030 C1 describes a method for determining the thickness of a layer in the case of overlapping echo impulses. In this, the build-up time of the detected enveloping curve is used as a measure for the layer thickness. To this effect, the measuring device must first be calibrated by means of measurements on layers of known thickness by storing a correlation between build-up time and layer thickness. The necessity of such demanding calibration presents a first disadvantage of this method. A further disadvantage arises from the fact that a layer can only be measured from the direction of the substrate side which in most cases is not accessible. This places extreme limits on the application range of this method. In addition, the method only functions for strongly overlapping echo impulses of amplitudes similar in size, which presents a further serious limitation.

Published application DE 44 34 688 A1 discloses an ultrasound thickness-gauging device with digital data acquisition and an evaluation unit which subjects the echo impulses to an evolution analysis. Evolution takes place by means of a division in the frequency domain (Wiener filtering). Fast Fourier transformation (FFT) or inverse FFT is used for the transition from the time domain to the frequency domain and back. Evolutions in the frequency domain suffer from the disadvantage of being very sensitive to unknown noise present in the spectrum of the measuring signal.

Both the above-mentioned documents describe ultrasound thickness-gauging devices which operate only in contact with the object to be measured or by means of a special coupling medium, but not in a non-contacting way. However, non-contacting thickness-gauging would be desirable for various applications, for example to avoid leaving any traces on the objects to be measured; to avoid damaging the objects to be measured; or to avoid their contamination by a coupling medium. Gauging the thickness of a freshly applied layer of powder, lacquer or paint, prior to baking, drying or hardening provides one example where only a non-contacting method of measurement can be considered.

It is the object of the present invention to describe a method for characterising objects to be measured by means of ultrasound, in particular for thickness-gauging, measuring the acoustic velocity, or measuring a surface profile. The method is to be suitable for non-contacting or contacting measurements, according to choice. It is to be applicable to objects with thicknesses or steps below, equal to, or above the sound-wave length used. For example a homogenous object, a self-supporting layer system or one or several layers on a substrate may be an object to be measured. In the latter case, the measuring method should be able to be applied from the direction of the side with the layer or the substrate, according to choice. Furthermore, it is the object of the present invention to provide a measuring device for implementing the method.

This object is met by the measuring method according to the invention and by the measuring device according to the invention, as defined in the independent claims.

With the measuring method according to the invention, at least one ultrasonic wave is transmitted by a measuring device; echo waves reflected by the boundary surfaces of the object to be measured are detected as a measuring signal by the measuring device. The measuring signal is digitalised and subjected to an evolution analysis in the time domain. The evolution algorithm used is based on the assumption that the quantity of "physically sensible" reflection sequences can be limited by using realistic a-priori value ranges orientated towards the test problem. The measuring signal is taken to be a convolution of a reflection sequence depending on the object to be measured, with a system reply depending on the measuring system. This approach in the time domain leads to a tree-based maximum-likelihood sequence estimation of exponentially increasing complexity. However, in the case of real interesting definitions of the problem, this complexity can be reduced by incorporating existing a-priori values orientated towards the test problem, and by respective data concerning the reflection sequence.

The measuring method according to the invention uses a new evolution algorithm in the time domain which is particularly computation efficient by orthogonalisation and by an implemented search strategy corresponding to the existing a-priori value ranges. In the evolution algorithm according to the invention, a given measuring signal is approximated by weighted additive overlapping of temporally shifted base impulses (wavelets). The shape of the base impulse can be derived from suitable reference signals (calibration, gauging) and is taken as being known. In this, dispersion and frequency-dependent acoustic decay can be considered by a shape of the base impulses changeable with the delay time. Weighting and temporal shift of the base impulses is for example optimally determined in the least-square-sense, i.e. by minimising the error square sum (sum of the squares of the differences between measuring signal and evolved signal). However, other optimisation algorithms may also be used for this purpose. In the case of white measuring noise, this represents the solution with the largest probability; the so-called maximum likelihood solution.

When characterising another object to be measured, the characteristics of an object to be measured can be further used in a predicative way as a-priori values orientated towards the test problem. In the measuring method according to the invention, the a-priori values can be used recursively or in the shape of a stepped range sequence. In this way, the present invention constitutes a self-learning measuring device in the sense of an expert system.

The measurement method according to the invention achieves accuracy of calculation and measuring exceeding the real rate of digitalisation, in that in the evolution analysis the real digitalisation rate is computationally separated from the measuring resolution. The maximum achievable resolution of the delay time measurement is thus not limited by the real digitalisation rate. Irrespective of the desired and thus in part higher measurement resolution, the underlying real digitalisation rate must only fulfil the known Nyquist theorem, i.e. it must be larger than, or equal to, the twofold useful bandwidth of the measuring signal. By means of the search and evolution algorithm according to the invention, the interesting reflection sequences specific to the object to be measured can be derived even in the case of strongly overlapping echoes, as so-called spike trains (pulse train, sequence of discrete individual results, infinitely sharp peaks). By means of suitable threshold values and simple combinations, in this way the interesting delay time can be accurately measured from the pulse train, and relevant characteristics of the object to be measured can be determined by means of calibration.

For non-contacting characterisation of objects to be measured, the measuring method according to the invention uses transducer units in the measuring device which are optimised for air ultrasound. In the case of coating materials of relatively low acoustic impedance (for example non-baked powder or non-dried wet lacquers), while part of the incident acoustic energy is reflected at the boundary surface between air and the layer, nevertheless a component of the energy that is sufficiently large for measuring purposes penetrates the non-hardened coating material. The transition to the (for example metallic) substrate again represents a significant increase in impedance which reflects a large proportion of the energy. With the method according to the invention, the delay time difference of the two echo impulses can be determined precisely.

As described above, the layer thicknesses, acoustic velocities or step heights are directly correlated with the delay-time difference and are directly determined from the delay-time difference.

On the other hand, the measuring method according to the invention also allows measurement right through a coupling medium or in direct contact with the object to be measured. In this case the transducer unit of the measuring device needs to be adapted accordingly.

The method according to the invention allows operation in the impulse-echo mode or in the transmit-receive mode. In the impulse-echo mode, ultrasound transmitter and ultrasound receiver are realised in a single transducer unit; in the transmit-receive mode a first transducer unit is employed as an ultrasound transmitter and a second transducer unit as an ultrasound receiver.

The applications for the method according to the invention are manifold. For example it can be used for thickness gauging, materials testing and fault detection in the case of concrete and building materials in general. It is well suited for infrastructure constructions such as pipes. In particular it can also be employed in the case of materials which are difficult to expose to ultrasonic waves, for example metals, where only low ultrasound frequencies can be employed due to high absorption at high frequencies. In addition, the method according to the invention can be employed for thickness gauging of all kinds of coatings, for example for lacquer or paint coatings, ceramic coatings and plasma coatings. Thus not only the thickness of individual layers but also the thickness of several layers of a layer system can be determined. Correspondingly, the method according to the invention is also suitable for composite layer materials for example those used for pressure vessels; the individual layers may be made of metal, plastic, ceramic or other materials. It is also possible to measure steps on surfaces or surface profiles.

Essentially the measuring device according to the invention comprises the following components which can be optimised to the respective actual measuring problem: at least a transducer unit, a transmitter unit, a receiver unit, an analogue-digital transducer unit and a microprocessor system with memory. If required a display unit, an input unit and/or a memory unit may be added.

Figure 2:
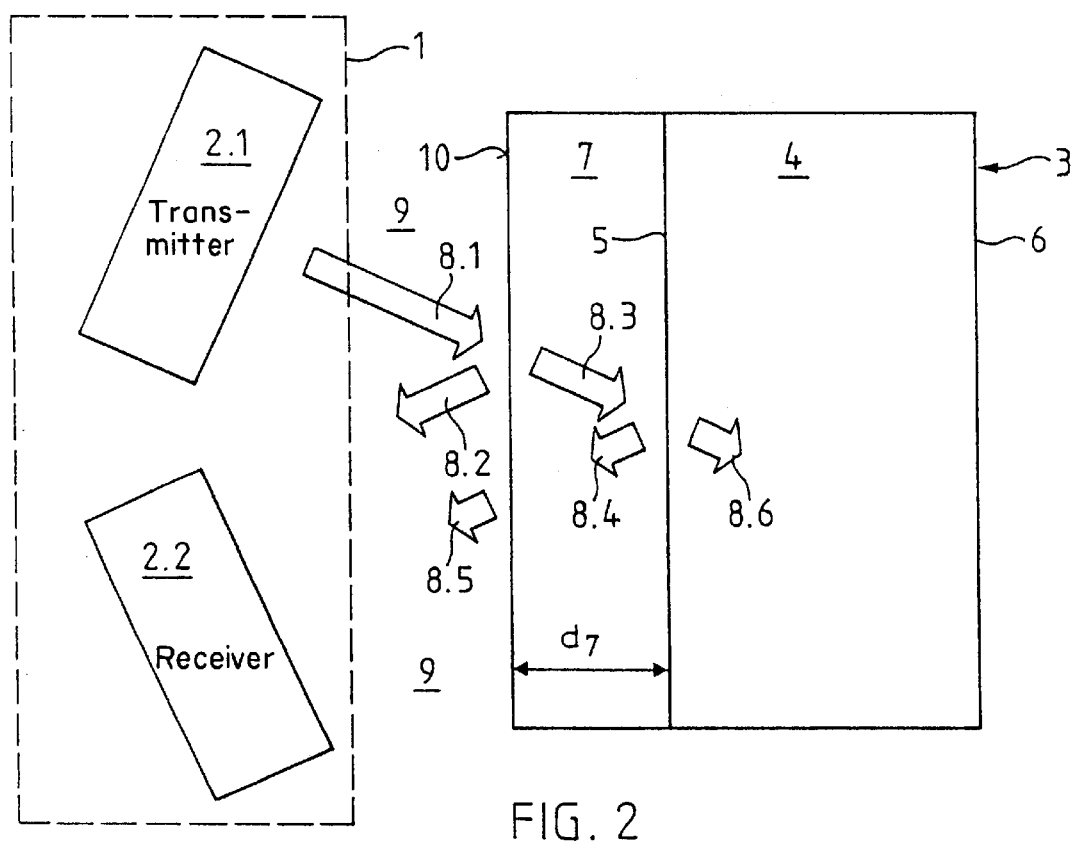
Figure 3:
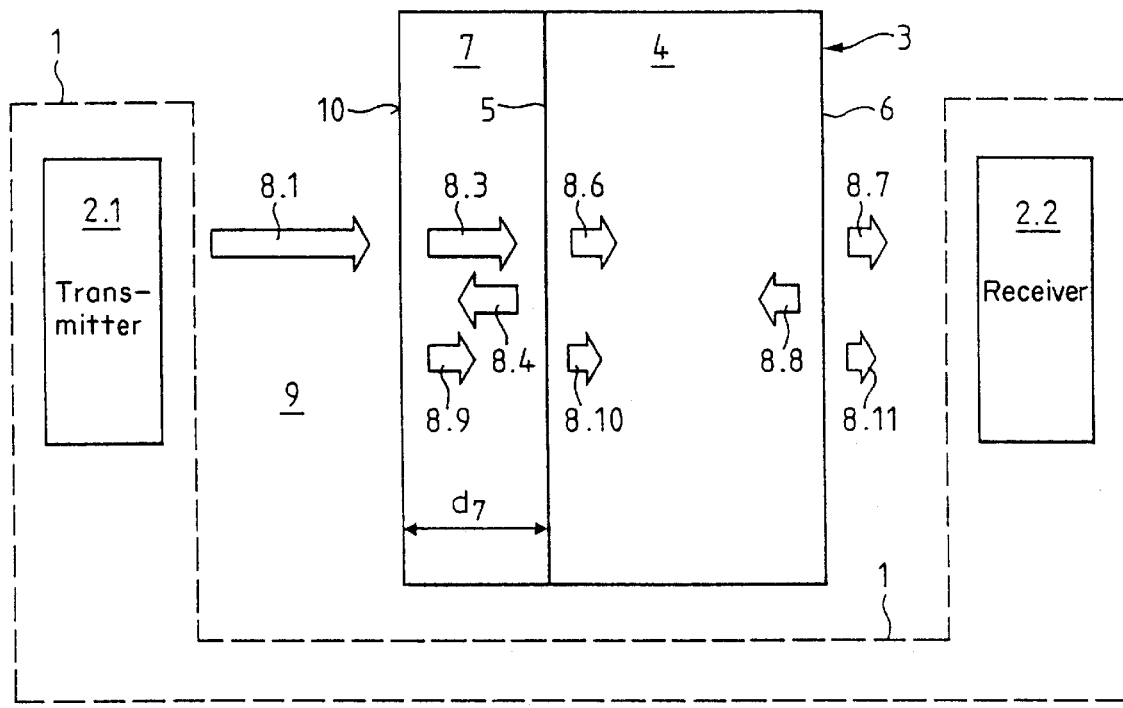
Figure 9:
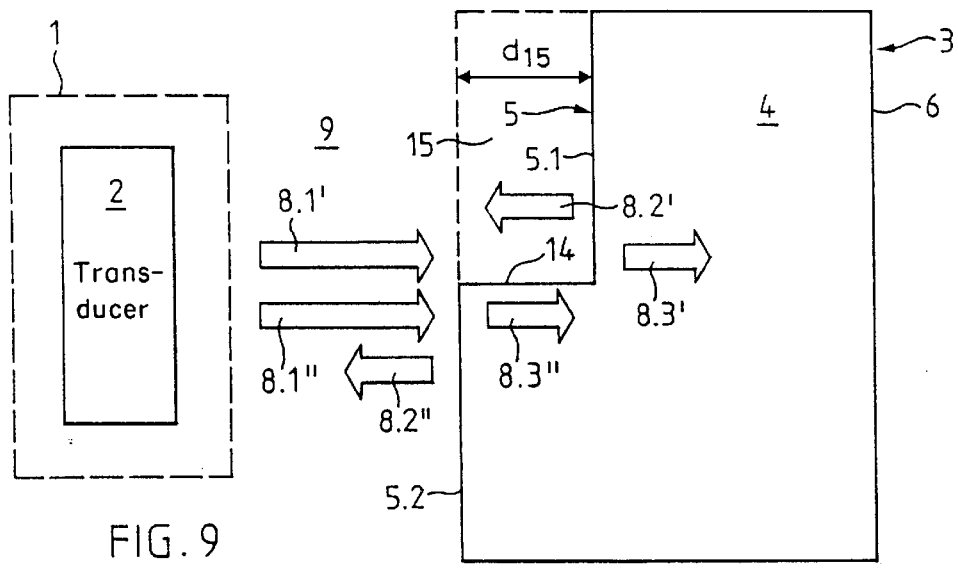
Figure 4:
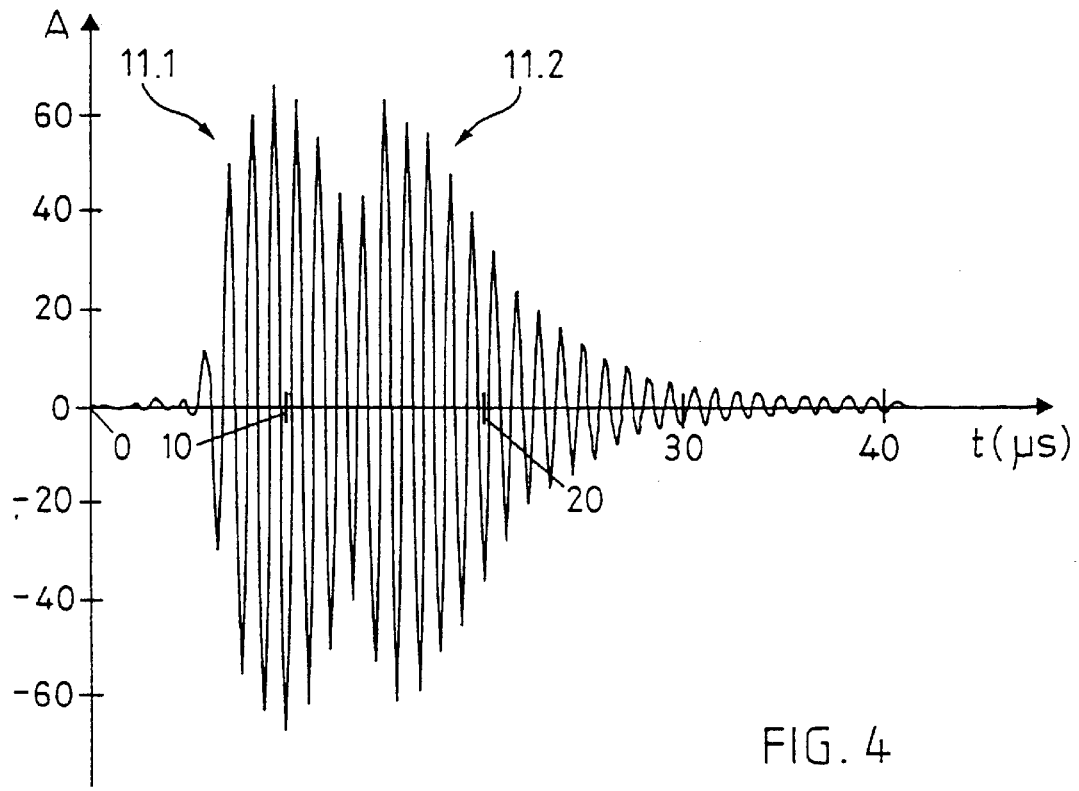
Figure 5:
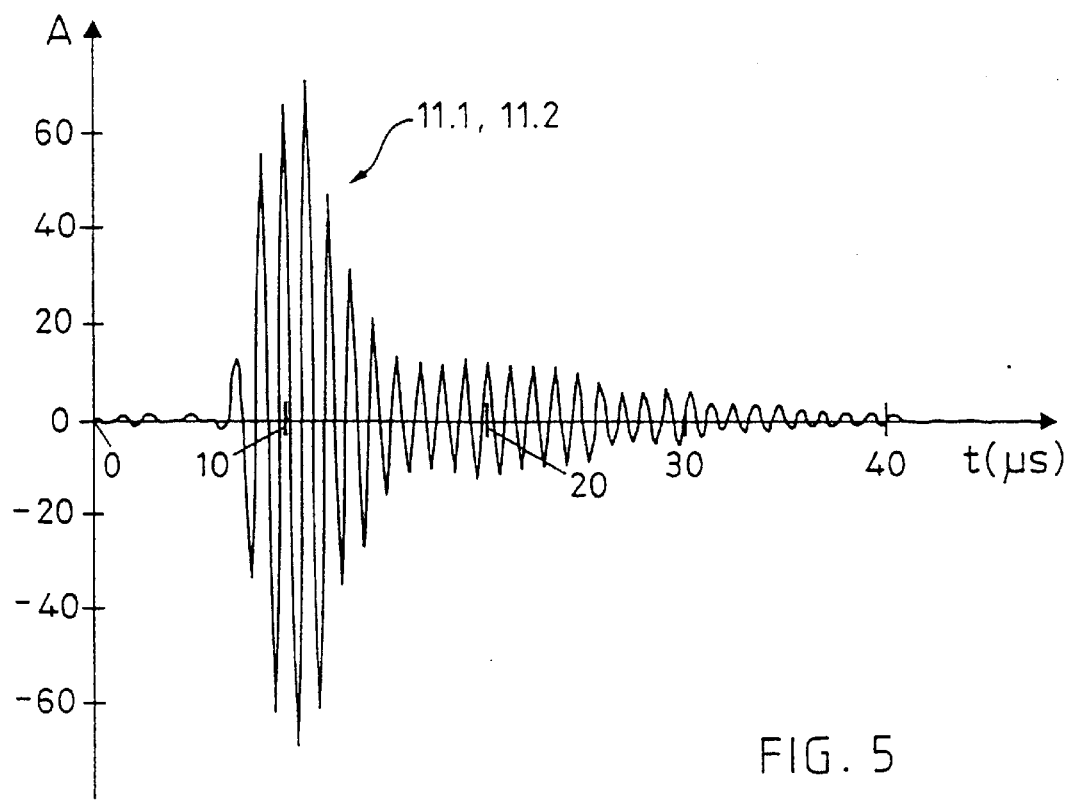
Figure 6:
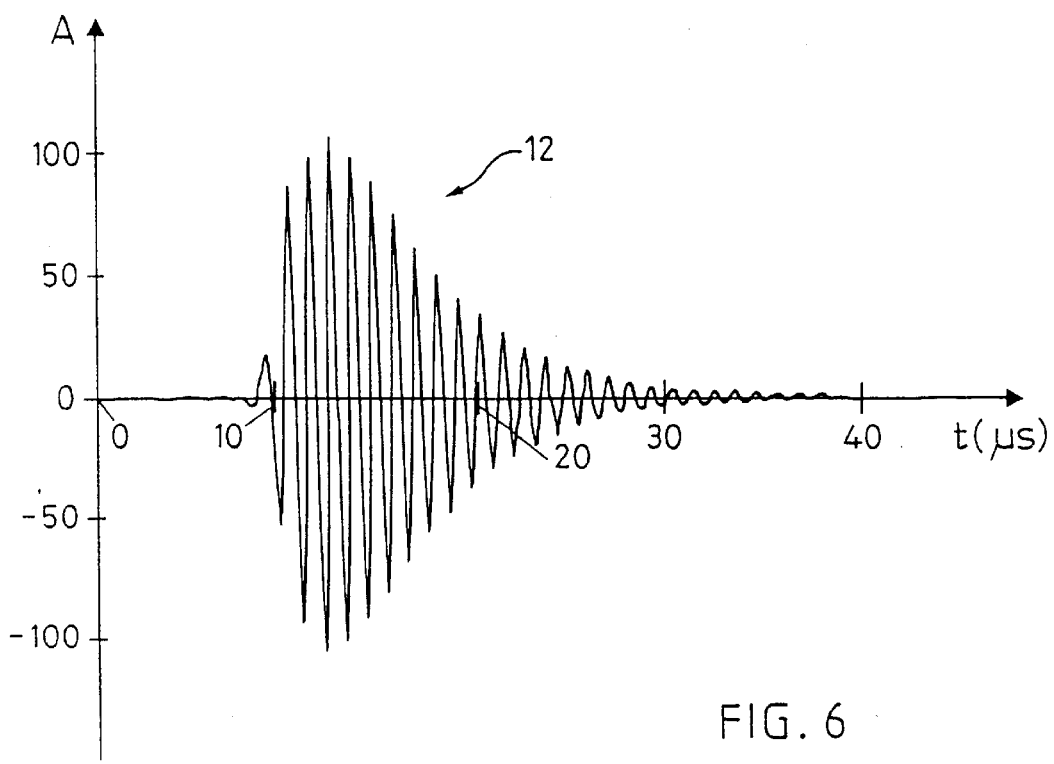
Figure 10:
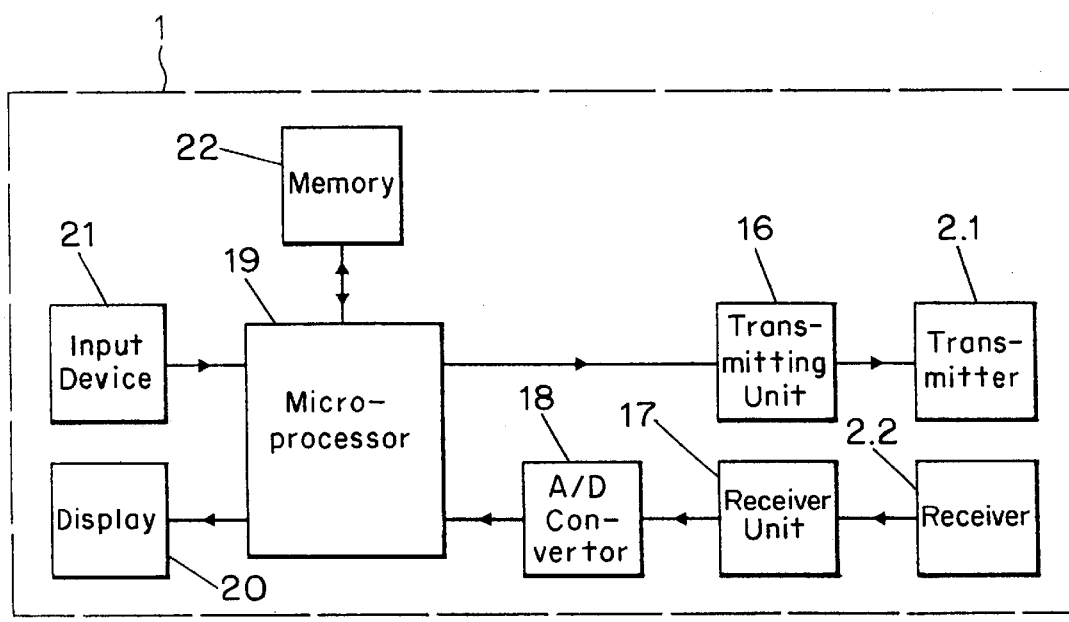
Figure 7:
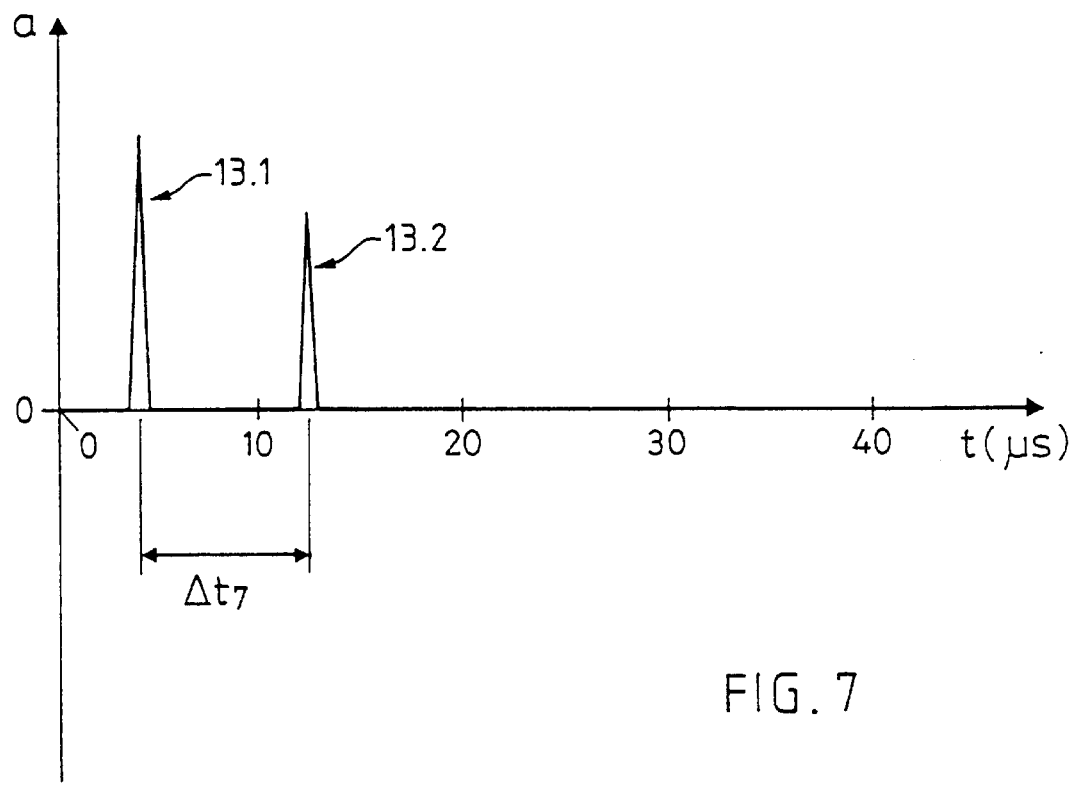
Figure 8:
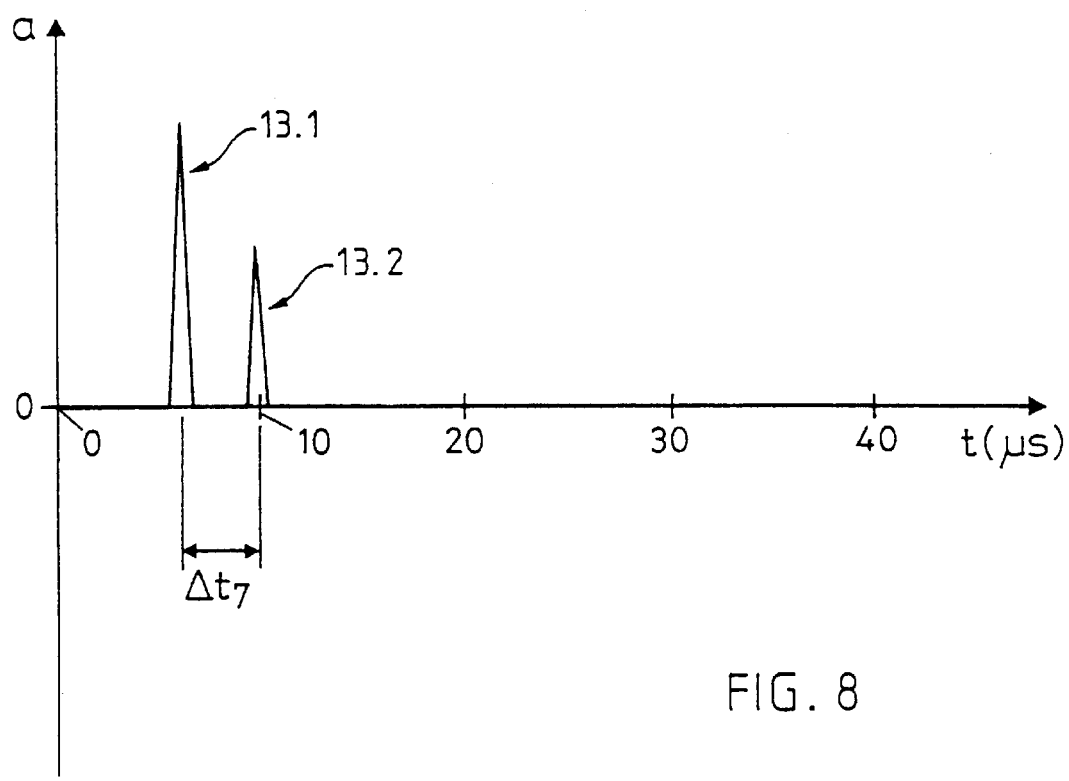
Figure 11:
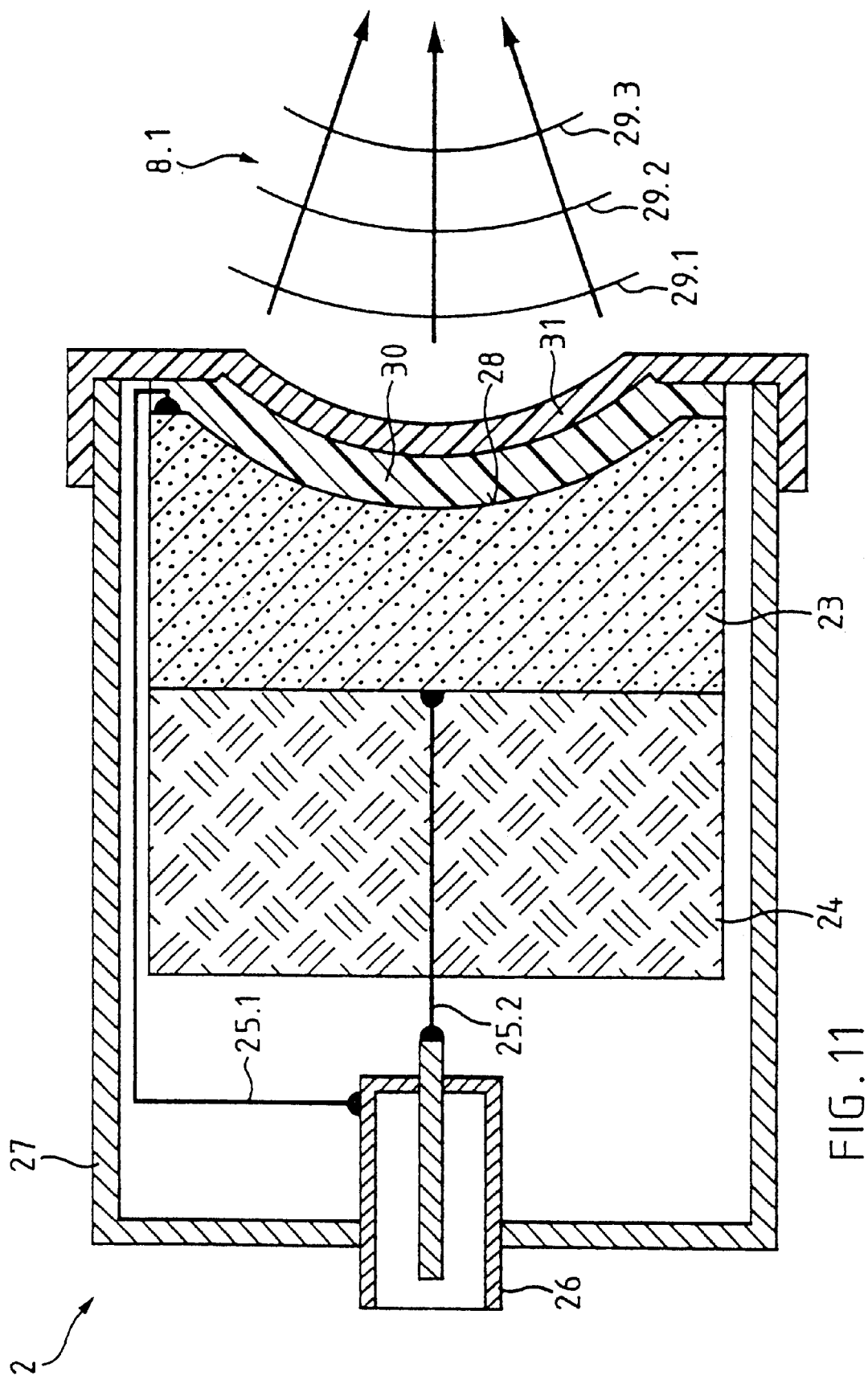

Below, the invention is shown in detail by means of Figures. The following are shown:

FIG. 1–3 exemplary set-up of measuring arrangements of the measuring method according to the invention;

FIGS. 4 and 5 typical measuring signals of echo impulses;

FIG. 6 a typical measured base impulse;

FIGS. 7 and 8 typical signals evolved with the evolution algorithm according to the invention;

FIG. 9 a set-up of measuring arrangements for measuring steps on a surface;

FIG. 10 a block diagram of an embodiment of a measuring device according to the invention; and FIG. 11 a diagrammatic cross section through a transducer unit of a measuring device according to the invention.

FIG. 1 shows an exemplary set-up of measuring arrangements of the measuring method according to the invention. A measuring device 1 with a transducer unit 2 transmits and receives ultrasonic waves, depicted by arrows, whose direction indicates the direction of propagation and whose length approximately indicates the energy or the amplitude of the respective ultrasonic wave. A measuring object 3 for example comprises a substrate 4, on whose front 5 and/or back 6 layers to be measured are located. In the example shown, substrate 4 only comprises one layer 7 with a thickness $d_7$ at the front 5. An ultrasonic wave 8.1 transmitted by the measuring device 1, preferably a short ultrasound impulse, travels towards the object 3 to be measured through a surrounding medium 9 (for example air). Generally, the incident ultrasonic wave 8.1 is partly reflected at the boundary surface 10 between the surrounding medium 9 and the layer 7; the reflected ultrasonic wave 8.2 travels back to the measuring device 1 as an echo wave or echo impulse. A transmitted part 8.3 of the incident ultrasonic wave travels through the layer 7 towards the substrate 4 (or, if present, towards a second layer, not shown). If the acoustic impedance of the layer 7 and the substrate 4 (or if present, a second layer) is different, then again part of the ultrasonic wave is reflected, and so forth. In this way, several echo waves or echo impulses 8.2, 8.5 are generated, which are detected by the measuring device 1 as a measuring signal as a function of time.

The set-up of measuring arrangements shown in FIG. 1 measures in the impulse-echo-mode, i.e. the measuring device 1 is equipped with a single transducer unit 2 which at first as an ultrasound transmitter transmits the ultrasonic wave 8.1 and subsequently as an ultrasound receiver receives the echo waves 8.2, 8.5.

By contrast to FIG. 1, FIG. 2 shows a set-up of measuring arrangements which measures in the transmit-receive mode. The measuring device 1 comprises two transducer units 2.1, 2.2; a first transducer unit 2.1 is employed as an ultrasound transmitter and a second transducer unit 2.2 is employed as an ultrasound receiver.

FIG. 3 shows a third set-up of measuring arrangements which (as is the case in the set-up of measuring arrangements in FIG. 2) measures in the transmit-receive mode, in this case however the object 3 to be measured is investigated by ultrasonic transmission. Here too, a first transducer unit 2.1 transmits ultrasonic waves 8.1; echo waves or echo impulses 8.7, 8.11 result at the boundary surfaces of the object to be measured and are received by the second transducer unit 2.2. The method according to the invention can also be employed in conjunction with other measuring modes.

On the one hand, air can be used as a medium 9 between the measuring device 1 and the object 3 to be measured; on the other hand another coupling medium with suitably selected acoustic impedance may also be used. For many applications, air is preferred, particularly if the object 3 to be measured might be damaged or contaminated by a coupling medium. The coupling medium need not be at rest; for example it is possible to measure right through one or several water jets which are emanating from the direction of the measuring unit 1 towards the object 3 to be measured.

FIG. 4 shows a typical progression of the amplitude A (for the sake of simplicity comprising only two echo impulses 11.1, 11.2) of a detected measuring signal A(t) as a function of time t. For the following reasons, interpretation of such a measuring signal A(t) is problematic. The large widths of the echo impulses 11.1, 11.2 render exact determination of their position difficult. Still, in the present example the two echo impulses 11.1, 11.2 can be distinguished from each other in a fashion. However, in the case of thin objects 3 to be measured, measuring signals A(t) may occur where the echo impulses seem to coincide and are hardly distinguishable from each other. FIG. 5 shows such a measuring signal A(t), in which it is no longer possible with the naked eye to distinguish between two different ultrasound impulses 11.1, 11.2. Nevertheless, with the measuring method according to the invention, the interesting reflection sequences can be obtained as sharp peaks. With known methods, the thickness of the thin object 3 to be measured or the acoustic velocity in the thin object 3 to be measured could only be determined without certainty, and from the measuring signal A(t) only inaccurately or not at all.

In the measuring method according to the invention, the detected signal A(t) is interpreted as a convolution of a known system reply dependent on the measuring system, with a sought reflection sequence depending on the object to be measured. In addition, the measuring signal A(t) contains additive noise as a disturbance. By means of a suitable evolution algorithm, the measuring signal A(t) is now evolved to obtain the sought reflection sequence. The evolution algorithm used is based on the premise that the quantity of "physically sensible" reflection sequences can be limited by using realistic a-priori value ranges orientated towards the test problem. By orthogonalisation and by an implemented search strategy in the time domain, corresponding to the existing a-priori value ranges, the evolution algorithm is particularly computation efficient.

The measuring signal A(t) is approximated by weighted additive overlapping of temporally shifted base impulses 12 (wavelets). The shape of the base impulses 12 can be derived from suitable reference signals. FIG. 6 shows an example of a measured base impulse 12; it is the average of several reference measurements of echo impulses which resulted from reflection at a flat steel surface. Weighting and temporal shift of the base impulses 12 is preferably optimally determined by minimising the error square sum (least square) in relation to the measuring signal A(t), i.e. the sum of the squares of the differences between measuring signal A(t) and calculated signal is determined. However, other optimisation algorithms which are known per se may also be used. The accuracy of calculation and measuring exceeds the real digitalisation rate; thus under certain circumstances the thickness resolution is only a fraction of the length of the ultrasonic wave used in the object to be measured. By means of suitable threshold values and simple combinations, the interesting delay time is exactly measured from the measuring signal, and relevant characteristics of the object to be measured such as material thickness, acoustic speed or step height are determined from the measuring signal by means of calibration.

FIGS. 7 and 8 show signals a(t) evolved according to the invention, i.e. amplitudes a are shown in temporal function t which may for example correspond to the measuring signals of FIGS. 4 or 5. Essentially they comprise sharp peaks 13.1, 13.2 which correspond to the echo impulses of the different boundary surfaces of the object 3 to be measured. Thus for example the first peak 13.1 corresponds to the echo impulse 8.2 of the boundary surface between the surrounding medium 9 and the layer 7; the second peak 13.2 corresponds to the echo impulse 8.5 of the boundary surface between the layer 7 and the substrate 4, and so forth. Positive amplitudes a >0 correspond to transitions between a medium of small acoustic impedance and a medium with greater acoustic impedance; negative amplitudes a <0 correspond to the opposite case. Essentially the amount |a| of the amplitudes is given by the ratio of the acoustic impedance at a boundary surface and by the acoustic decay experienced by the ultrasonic wave. Due to the sharpness of the peaks 13.1, 13.2, their positions on the time axis can be clearly determined. The spaces between the peaks correspond to the delay time differences $\Delta t_i$. When the acoustic speeds $c_i$ are known, the sought layer thickness $d_i$ can be calculated from the said delay time differences according to the formula $$d_i = c_i \Delta t_i / 2.$$

In each instance the index i denotes a medium or a layer of the object 3 to be measured, for example $d_7$ is the thickness of the layer 7 shown in FIGS. 1–3. Where the layer thicknesses $d_i$ are known, of course the acoustic speeds $c_i$ can be determined from the evolved signal a(t).

The thickness-gauging range of the measuring method according to the invention is very large. Downward the measuring range is limited by the resolution of the measuring method. As described above, the resolution limit is somewhat smaller than the length of an ultrasonic wave in the object 3 to be measured. Upward, the measuring range is limited by absorption in the object 3 to be measured. However as long as an echo signal of sufficiently high amplitude can still be detected, it is possible with the method according to the invention, also to evaluate measuring signals A(t) where the echo impulses are distanced far apart in comparison to their half width. In general in the case of materials which have a strongly decaying influence on ultrasound, such as for example metal casting, masonry work etc., preferably low ultrasound frequencies are used to keep absorption within limits. By contrast, in the case of materials which have a lightly decaying influence on ultrasound, such as for example ceramics, preferably high frequencies are used to achieve as high a resolution as possible. Advantageously, the width of the ultrasound impulses used is matched to the measuring problem.

FIG. 9 diagrammatically shows a special embodiment of the measuring method, analogous to FIG. 1. This is an application for measuring steps 14 on a surface 5 of an object 3 to be measured. The step 14 to be measured divides the surface 5 of the object 3 to be measured, into a first partial surface 5.1 and a second partial surface 5.2. The ultrasonic wave is transmitted onto the surface 5 of the object 3 to be measured in such a way that a first part 8.1' of it hits the first partial surface 5.1 and a second part 8.1" of it hits the second partial surface 5.2. The first part 8.1' and the second part 8.1" of the ultrasonic wave are partially reflected by the partial surfaces 5.1, 5.2 and the reflected partial waves 8.2', 8.2" are detected and evaluated as described above. Actually this embodiment of the method also employs thickness gauging with the thickness $d_{15}$ of a virtual air layer 15 being measured above the first partial surface 5.1. A step 14 shown in FIG. 9 only represents a special case of a three-dimensional structure on a surface 5 of an object 3 to be measured. Analogous to the step measurement described above, the method according to the invention allows measuring in a more general way, of a surface profile of an object 3 to be measured.

FIG. 10 diagrammatically shows an exemplary block diagram of a measuring device 1 according to the invention. The measuring device 1 for example contains two transducer units 2.1, 2.2 which convert electrical energy into ultrasonic energy and/or vice versa, for example piezoelectric transducers. As shown in the example of FIG. 1, the measuring device 1 may also be equipped with only one transducer unit 2; it can also be advantageous to employ more than two transducer units. A transmitting unit 16 supplies the necessary electrical signals to the first transducer unit 2.1. The transmitting unit 16 can for example generate a rather broad-band discharge pulse (spike), a rather narrow-band unipolar or bipolar square pulse sequence (toneburst) or a purposefully controlled or formed transmission impulse. A receiver unit 17 comprises analogue filters and amplifiers; the latter can for example provide linear or logarithmic amplification. In an analogue-digital transducer 18, the analogue electrical signal received is converted into a digital signal. For control and evaluation, preferably a microprocessor system 19 with a memory (not shown) is used.

In particular in those applications where the measuring unit 1 is used autonomously, it is preferably equipped with a display unit 20, for example a display, a monitor or a printer, and/or an input device 21, for example a keyboard. The display unit 20 and the input unit 21 are used for data exchange between the measuring device 1 and a user (not shown). In other applications the measuring device 1 according to the invention can be integrated into a larger system (not shown), for example a manufacturing robot. In this case the display unit 20 and the input unit 21 can be dispensed with and the data between the measuring device 1 and the system are exchanged via data lines which are known per se. Furthermore, the measuring device 1 may comprise an additional memory unit 22 for storing and archiving the measuring data. For example the a-priori values orientated towards the test problem may be stored in such a memory unit 22, and retrieved from it for evolution of subsequent measurements.

FIG. 11 is a cross section through a simple embodiment of a transducer unit 2 of a measuring device 1 according to the invention. The transducer unit 2 comprises one or several ultrasound transducers 23 for converting electrical energy to ultrasound energy and/or for converting ultrasound energy to electrical energy.

To this purpose for example the piezoelectric or magnetostrictive effect can be exploited; the transducer materials are selected accordingly. In particular for air ultrasound measuring devices it can be advantageous to use a composite ultrasound transducer which can be adapted to the respective application. The ultrasound transducer 23 is preferably attached to an attenuation body 24 which mechanically attenuates the ultrasound transducer 23 and thus makes it possible to generate short ultrasound impulses. Electrical signal lines 25.1, 25.2 connect the ultrasound transducer 23 with a connecting socket 26. The electrical signal lines 25.1, 25.2 may comprise means (not shown) for matching the output of the ultrasound transducer 23, for example a matching coil. Furthermore, the transducer unit 2 comprises a housing 27.

To influence the directions of propagation and/or the wave shapes of the ultrasonic waves, the ultrasound transducer 2 may comprise at least one inclined plane surface and/or at least one curved surface. In the example in FIG. 11, the front surface 28 is spherically curved inwards, resulting in a transmitted ultrasonic wave assuming the shape of an incoming spherical wave, i.e. it is focussed. Such a transmitted spherical wave 8.1 is diagrammatically shown in FIG. 11 with some of its phase surfaces 29.1, 29.2, 29.3.

To optimise the transducer unit 2, the ultrasound transducer 23 may comprise a matching layer 30 of suitable acoustic impedance. One or several boundary surfaces of the matching layer may be inclined or curved; possibly differently from the ultrasound transducer 23. In this way in turn directions of propagation and/or wave shapes of ultrasonic waves may be influenced; for example an ultrasonic wave may be focussed by way of a spherical boundary surface of a matching layer 30. A protective layer 31 may protect the various elements 23–27, 30 of the transducer unit 2 from undesirable external physical and/or chemical influences.

In summary, in the method according to the invention for characterising objects 3 to be measured by means of ultrasound, at least one ultrasonic wave 8.1 is transmitted by a measuring device 1. Echo waves 8.2, 8.5, reflected by boundary surfaces (5, 10) of the object 3 to be measured are detected by the measuring device 1 as a measuring signal A(t). Characteristics of the object 3 to be measured are determined from delay time differences Δt of the echo waves 8.2, 8.5, by the measuring signal A(t) being digitalised and in the time domain being subjected to an evolution analysis delimited by a-priori value ranges orientated towards the test problem, by weighted additive overlapping of temporally shifted base impulses 12. A measuring device 1 according to the invention, for implementing the method, comprises at least one transducer unit 2 which comprises at least one ultrasound transducer 23 for converting electrical energy to ultrasound energy and/or converting ultrasound energy into electrical energy; an ultrasound transmitting unit 16 to supply the transducer unit 2 with electrical signals; an ultrasound receiver unit 17; an analogue-digital transducer unit 18 for converting an analogue electrical signal into a digital signal and a microprocessor system 19 for control and evaluation.

What is claimed is:

1. A method for characterizing an object with boundary surfaces by means of ultrasound, comprising the steps of
    a) determining a time dependent base impulse from reference signals,
    b) creating at least one ultrasonic wave in said object,
    c) detecting echo waves reflected by said boundary surfaces, thus determining a time dependent measuring signal,
    d) digitalizing said time dependent measuring signal,
    e) creating a time dependent calculated signal as the sum of temporally shifted and weighed modifications of said base impulse,
    f) evaluating the sum of the squares of the differences between said measuring signal and said calculated signal,
    g) repeating evolution steps e) and f) until one optimal calculated signal is found, for which said sum of the squares of the differences between the measuring signal and the calculated signal is minimized, and
    h) determining a measurement result from the temporal shifts and weightings of this one calculated signal.

2. A method according to claim 1 wherein the base impulse is determined from a calibration or gauging measurement.

3. A method according to claim 1 wherein, depending on the delay time and thus on the material depth, an adapted base impulse is used.

4. A method according to claim 1 wherein an orthogonalization and an implemented search strategy are used for the evolution steps, thus making the computation efficient.

5. A method according to claim 1 wherein the characteristics of an object to be measured are used for the evolution steps.

6. A method according to claim 1 wherein the real digitalization rate is comptitationally separated from the measuring resolution, thus achieving accuracy of calculation and of measuring which exceeds the real rate of digitalization.

7. A method according to claim 1 wherein ultrasonic waves propagate in air between a measuring device and said object to be measured.

8. A method according to claim 1 wherein ultrasonic waves propagate in at least one contact medium between a measuring device and said object to be measured.

9. A method according to claim 1 wherein ultrasonic waves propagate in at least one water jet between a measuring device and said object to be measured.

10. A method according to claim 1 wherein thicknesses are determined from known acoustic velocities in said object to be measured and from evaluated optimal temporal shifts.

11. A method according to claim 1 wherein from known object thicknesses and from evaluated optimal temporal shifts, acoustic velocities are determined.

12. A method according to claim 1 wherein heights of steps on the surface of said object to be measured are determined.

13. A method for characterizing, an object with boundary surfaces by means of ultrasound, comprising the steps of
    a) determining a time dependent base impulse from reference signals,
    b) creating, at least one ultrasonic wave in said object,
    c) detecting echo waves reflected by said boundary surfaces, thus determining in a time dependent measuring signal,
    d) digitalizing said time dependent measuring signal,
    e) creating a time dependent calculated signal as the sum of temporally shifted and weighed modifications of said base impulse,
    f) evaluating a measure for the difference between said calculated signal and said measuring signal,
    g) repeating evolution steps e) and f) until one optimal calculated signal is found, for which said measure for the difference between said calculated signal and said measuring signal is minimized, and
    h) determining a measurement result from the temporal shifts and weightings of this one calculated signal,
wherein orthogonalization is used for creating the time dependent calculated signal.

14. A measuring device characterizing an object with boundary surfaces by means of ultrasound, comprising a transducer unit or a plurality of transducer units with ultrasound transducer means for converting electrical energy to ultrasound energy, an ultrasound transmitter unit to supply said transducer unit with electrical signals, an ultrasound receiver unit for receiving echo waves reflected by said boundary surfaces, and means for convicting, ultrasound energy contained in said echo waves to electric energy thus determining a time dependent measuring signal, a storage means for storing a digital representation of a time dependent base impulse from reference signals, an analogue-digital transducer unit for digitalizing said time dependent measuring signal, a microprocessor system possessing a code for control and evaluation, such code configured to make the microprocessor system carry out the following evaluation steps:
    a) creating a time dependent calculated signal as the sum of temporally shifted and weighed modifications of said base impulse,
    b) evaluating the sum of the squares of the differences between said measuring signal and said calculated signal,
    c) repeating evolution steps e) and f0 until one optimal calculated signal is found, for which said sum of the squares of the differences between the measuring signal and the calculated signal is minimized, and
    d) determining a measurement result from the temporal shifts and weightings of this one calculated signal.

15. A measuring device according to claim 14 which comprises at least one piezoelectric or magnetostrictive ultrasound transducer.

16. A measuring device according to claim 15 comprising at least one composite ultrasound transducer.

17. A measuring device according to claim 14 wherein at least one ultrasound transducer comprises at least one of an inclined plane surface section and a curved surface section for influencing directions of propagation or wave shapes of ultrasonic waves or both.

18. A measuring device according to claim 14 wherein at least one ultrasound transducer comprises at least one spherical surface for focusing ultrasonic waves.

19. A measuring device according to claim 14 wherein at least one ultrasound transducer comprises at least one matching layer of suitable acoustic impedance.

20. A measuring device according to claim 19 wherein at least one matching layer comprises at least one of an inclined plane surface section and a curved surface section for influencing directions of propagation or wave shapes of ultrasonic waves or both.

21. A measuring device according to claim 20 wherein at least one matching layer comprises at least one spherical surface for focusing ultrasonic waves.

22. A measuring device according to claim 14 wherein said ultrasound transducer transmitting unit comprises a means for generating a discharge pulse, a unipolar or bipolar square pulse sequence or a purposefully controlled transmission impulse.

23. A measuring device according to claim 14 wherein said ultrasound receiver unit comprises analogue filter stages and amplifier stages.

24. A measuring device according to claim 14 comprising a display unit and an input unit.

* * * * *